Figure 1A:
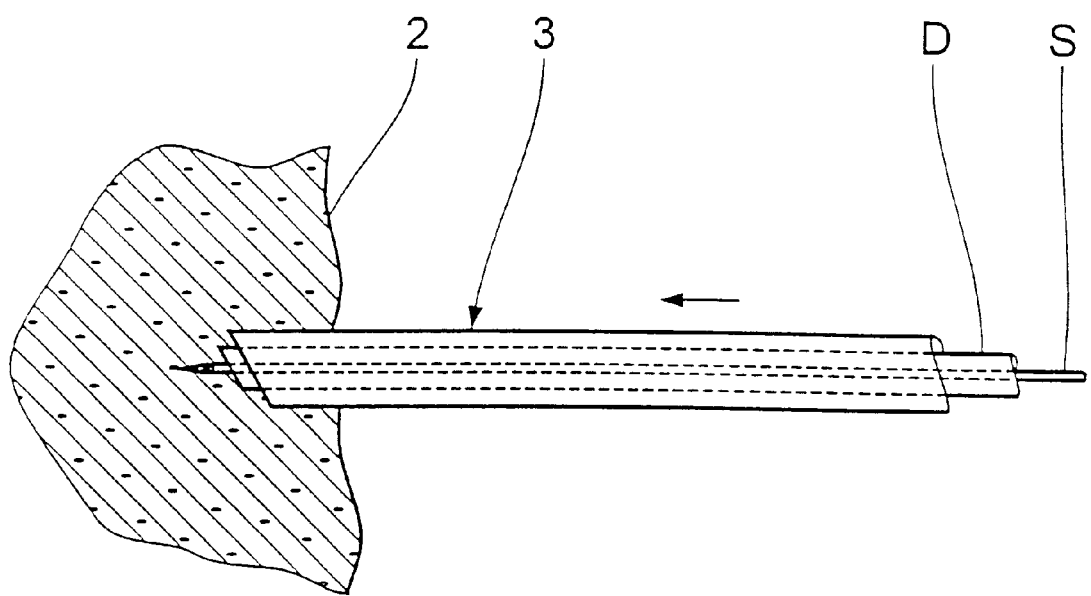

United States Patent [19]
Beuthan et al.

[11] Patent Number: 6,143,018
[45] Date of Patent: Nov. 7, 2000

[54] METHOD AND DEVICE FOR THERMALLY OBLITERATING BIOLOGICAL TISSUE

[75] Inventors: Jürgen Beuthan; André Roggan; Gerhard Müller, all of Berlin, Germany

[73] Assignees: CeramOptec GmbH; Hüttinger GmbH, both of Bonn, Germany

[21] Appl. No.: 08/545,864

[22] PCT Filed: May 11, 1994

[86] PCT No.: PCT/DE94/00554

§ 371 Date: Mar. 28, 1996

§ 102(e) Date: Mar. 28, 1996

[87] PCT Pub. No.: WO94/26184

PCT Pub. Date: Nov. 24, 1994

[30] Foreign Application Priority Data

May 14, 1993 [DE] Germany .............................. 43 16 176
Feb. 2, 1994 [DE] Germany .............................. 44 03 134

[51] Int. Cl.[7] ..................................................... A61N 5/06
[52] U.S. Cl. .................................. 607/88; 607/92; 606/2; 606/10; 606/16; 606/17; 604/20
[58] Field of Search ............................ 606/2–19; 607/88, 607/89, 92; 604/20

[56] References Cited

U.S. PATENT DOCUMENTS

| | | | |
|---|---|---|---|
| 4,336,809 | 6/1982 | Clark | 606/3 |
| 4,612,938 | 9/1986 | Dietrich et al. | 606/12 |
| 4,676,231 | 6/1987 | Hisazami et al. | 606/14 |
| 5,489,279 | 2/1996 | Meserol | 604/20 |
| 5,571,151 | 11/1996 | Gregory | 607/88 |

*Primary Examiner*—David M. Shay
*Attorney, Agent, or Firm*—BJ Associates; Bolesh J. Skutnik

[57] ABSTRACT

A process is disclosed for thermally obliterating biological tissues by laser radiation introduced into the tissue by means of an optical waveguide. The laser radiation is scattered by means associated with the radiation output surface of the optical waveguide. A biocompatible, medium to highly visquous liquid which does not substantially absorb the laser radiation but scatters it, is injected into the tissue, forming a scattering fluid deposit around the radiation output surface which is not separated from the tissue and which allows the tissue to be heated in a controlled manner.

11 Claims, 10 Drawing Sheets

METHOD AND DEVICE FOR THERMALLY OBLITERATING BIOLOGICAL TISSUE

DESCRIPTION

The invention relates to a method of the type disclosed in the preamble to claim 1 and a device for performing the method.

It is known that laser radiation can be guided by means of optical waveguides, and the radiation transmitted in this manner can be introduced into biological tissue, either directly by means of the optical waveguide, transluminally or transcutaneously, or be additionally influenced purposefully in its distribution function by further measures—for example, by way of special catheters or endoscopes—and the radiation applied in this manner can be used to induce thermal or photochemical necroses. Since the mid-1970's it has been standard practice to introduce, for example, neodymium:YAG radiation into biological tissue in this manner and use the absorption of this radiation occurring in the tissue to heat the area of the tissue at the end of the fiber and thus effect coagulation necroses.

As dictated by the fact that the optical fibers employed have active diameters between 200 and 600 $\mu$m, a very high power density results at the fiber/tissue boundary surface, even with low power outputs of the laser. Therefore, the carbonization threshold of the tissue is exceeded very rapidly, with the consequence that the exiting laser radiation is additionally absorbed by the carbonization product and can no longer penetrate corresponding to the optical coefficients typical for the tissue. Even the most commonly-used operator can only succeed in producing coagulation necroses having a 5 to 7 mm diameter, which typically accompany a carbonization of the tissue touching the fiber.

The transcutaneous introduction of the optical fiber, the so-called "bare fiber," is usually effected in an operation using puncture sets, i.e. with hollow metallic needles and trocars. Transluminal application using suitable flexible catheters or endoscopes is effected as a continuation.

A method for interstitial laser therapy is described in U.S. Pat. No. 5,169,396, the feature which distinguishes this method being that direct contact of the end surface of the fiber with the tissue is prevented by the placement of a fluid deposit with a biocompatible fluid which absorbs the laser radiation at the end of the puncturing needle. The primary result is that the fiber-tissue boundary surface is no longer heated, but instead the light-absorbing fluid is heated, which in turn warms the surrounding tissue by means of heat conduction.

Although this procedure prevents primary carbonization at the end of the fiber, it has the considerable disadvantage that the transport of energy into the tissue is only effected by heat conduction, and therefore leads to very limited coagulation necroses in view of the large heat sink of the surrounding tissue. Moreover, the method has the considerable disadvantage that the pigments or chromophoric groups of the fluid which absorbs the laser radiation also decompose photochemically or thermally at the fiber end with the radiation outputs used and the power densities stipulated by them, causing uncontrollable side effects.

In an arrangement known from DE 40 41 234, an attempt is made to resolve the problem of carbonization at the fiber-tissue boundary surface by specially preparing the fiber end in such a way that the laser radiation no longer exits the fiber pro-degree with a very small exiting aperture, but is scattered radially outwardly in steps from the fiber over a lengthy segment. The distribution of the laser power on the surface of the applicator is made more even by additional measures which further increase radial scattering, such as the provision of a scatter dome.

The goal of the most homogeneous possible introduction of the laser radiation into the tissue can be achieved extensively with these measures, but the technological expenditures involved in preparing the fiber end and possibly a high-temperature-resistant, yet flexible cover catheter are considerable. An additional disadvantage of this laser scatter light applicator having a cover catheter is that by nature the tissue layer adjacent to the catheter is heated particularly rapidly by the light absorption, and thus coagulates; it has been seen that the coagulated tissue has a distinctly poorer transmittance for directed optical radiation in the wavelength range.

Disclosed in DE 42 11 526 A1 and DE 42 37 286 A1 is a device which operates with an active cooling inside the cover catheter, with the cooling fluid simultaneously taking over the task of additionally scattering the laser light. In a modification, it is provided that biocompatible cooling fluid can exit the cover catheter through preformed pores in the catheter, so carbonization and hence adherence to the adjacent tissue are avoided.

In this arrangement, laser power of more than 5W, typically 10 to 12W, can be used due to the active cooling, but a portion of the applied energy is simultaneously carried off unused because of the cooling. Since the biocompatible fluid is distributed rapidly in the tissue, relatively large quantities are required during a 10- to 20-minute treatment, which may lead to discomfort for the patient. Finally, only approximately spherical-symmetrical treatment zones can be realized with this method—as in the above-mentioned solutions. The treatment of diseased tissue areas which are lengthy but relatively narrow requires a multiple application by means of repositioning in the cover catheter, and, for example in the treatment of benign prostatic hyperplasia (BPH), leads to very long radiation periods of up to 40 minutes per prostate lobe.

The object of the invention is to refine a method of the type mentioned at the outset in such a way that tissue obliteration is permitted, with the efficient use of laser radiation and scattering fluid, in the largest possible and also non-spherical-symmetrical treatment zones; the invention further relates to a device for performing the method.

This object is accomplished by a method having the features of claim 1 and a device having the features of claim 2.

The invention includes the concept of creating a scatter region which is essentially stable during treatment and is adapted as precisely as possible in size and spatial shape to the requirements of treatment, the region being located in the area surrounding the exit surface of the laser radiation from a light waveguide, which serves in its conduction, into the tissue to be obliterated; essentially no absorption takes place in this region, but instead the most diffuse possible scattering of the laser radiation is effected. A scattering fluid deposit of sufficiently viscous fluid or a fluid mixture which is essentially transparent in the wavelength range of the employed laser radiation serves this purpose.

Because the fluid does not absorb the laser radiation, and the scattering processes represent pure phase scattering, the fluid is not heated significantly, which suppresses coagulation on the radiation exit surface to the tissue over an extended period of time—measured against the total irradiation time.

The method of the invention is based on the surprising realization that, due to prevention of primary coagulation at the scatter fluid/tissue boundary zone, the laser radiation propagating diffusely in the scatter fluid can penetrate more deeply into the tissue by a factor of 2 to 3, and therefore be absorbed in a clearly greater volume and heats this volume. After an irradiation time of several minutes, a concentric coagulation zone occurs in the depth of the tissue which prevents further sheer transport of radiation into the depth of the tissue, but which, because of an increased temperature, simultaneously forms a very large heat source in terms of volume for use in heat conduction for further thermal obliteration of the surrounding tissue.

The tissue surrounding the fluid deposit is first coagulated toward the end of treatment by means of an increase in the radiation power of the laser, and thus leads indirectly to additional heating of the cooling fluid, so that, because of the deposited fluid and the solid, established coagulation front, a heat source is present even after the laser has been shut off, which in turn further damages surrounding tissue, also in the subcoagulative region, by means of heat conduction according to the Arrhenius integral. In the procedure of the method, diameters of coagulation zones of up to 3 cm can be attained in this way; also occurring because of the subcoagulative, hyperthermic influence due to the heat conduction is a further necrosis having a radius of approximately an additional 5 to 7 mm, so that, overall, necrosis foci of up to 4 cm can be established in a controlled manner.

The disadvantages of using a hollow metallic needle described in U.S. Pat. No. 5,169,396 are advantageously avoided in that a biocompatible hollow needle material which does not absorb the laser radiation is used to introduce the optical fiber and the scattering fluid into the tissue. Variations of the thermoplastic PTFE family, polycarbonates, variations of HDPE and certain polyurethanes are considered as this material.

The operational procedure is selected such that access to the center of the area of tissue to be obliterated is first achieved with a probing needle; this procedure can take place with simultaneous radiological or ultrasonic monitoring. Next, depending on the size of the necrosis focus to be established later, one or more dilators is or are guided via this needle, with the last of the dilators being identical to the hollow needle which later guides the laser beam. The biocompatible, phase-scattering fluid is subsequently introduced into the tissue via this plastic dilator, which is open at the end.

The hollow needle used is purposefully configured such that it comprises essentially two assemblies, one of which is the puncturing needle itself to be brought in via a probing needle, and the second of which represents a fluid-tight Y-piece to be connected to this puncturing needle after removal of the probing needle; on the one hand, the fluid which scatters the laser light can be injected via this Y-piece, while on the other hand the light waveguide which guides the laser light can be advanced axially, in a defined and pre-adjusted manner, via a feed mechanism, by way of the Y-piece.

Of particular significance for the method is the fact that the viscosity of the fluid is adapted to the respective treatment situation so that a spatially suitably-defined fluid deposit is maintained for a sufficiently long irradiation time. This eliminates conventional biocompatible fluids such as physiological sodium chloride solution, because they have such a low viscosity that several 100 ml of fluid are required to maintain a deposit during typical treatment times of 10 to 20 minutes in the tissue types considered for this kind of therapy, such as for parenchyma, muscle, prostate, etc. This can be avoided by the selection of a suitable fluid viscosity.

In a simple and cost-effective manner, the fluid can comprise a mixture of 0.1 to 2 parts oil, 10 to 50 parts water and 50 to 80 parts glycerine, with the sum of the respective parts totalling 100. In a preferred embodiment, an oil-water-glycerine suspension is used which has the following ratio of ingredients: 80% glycerine, 18% water and 2% suspended oil droplets.

Moreover, a mixture of 1 to 30 parts water and 70 to 99 parts methyl cellulose—preferably methyl cellulose combined with a few percent physiological sodium chloride solution can be used.

Finally, a mixture of hyaluronic acid and Intralipid can also be used.

The numerical aperture of the light waveguide is to be selected depending on the size and geometrical shape of the deposit. Good results are achieved with numerical apertures between 0.2 and 0.6. The use of an increased numerical aperture offers a simple option of also using diode lasers of approximately 800 nm as an energy source.

In an advantageous embodiment, the fluid comprises an essentially transparent component and a highly light-scattering component, and the components are injected into the tissue by way of a concentric double-channel hollow needles in such a way that the transparent component is introduced by way of the inside channel and the highly light-scattering component is introduced by way of the outside channel, so that the highly light-scattering component envelopes the transparent component.

The transparent component can include glycerine and water, preferably in a ratio of ingredients of 80:20, and the highly light-scattering component can include oil and water, preferably with 1 to 5 parts oil in a 100-part mixture.

In a structurally simple refinement of this embodiment, the laser radiation can be introduced into the tissue by way of the fluid column of the transparent component in the inside channel, which column simultaneously serves as a light waveguide, with the introduction of the laser light possibly also being effected by way of a non-stationary fluid column—i.e., while further fluid is injected.

In order to optimize the introduction of the radiation into the fluid deposit, following injection of the fluid and formation of the deposit the light waveguide can be displaced to a predetermined extent in the distal direction and into the deposit.

In order to form longitudinally-extending treatment zones, the scattering fluid deposit is formed in an longitudinally-extending, particularly essentially ellipsoid or cylindrical shape, and/or a light waveguide arrangement is used which has a radiation surface formed in this manner.

In an advantageous embodiment, this arrangement has an optical fiber whose surface includes in a distal end segment a plurality of matted regions which follow one another consecutively in the longitudinal direction and are preferably annular, the end segment of the surface being provided with a transparent protective covering for the laser radiation. The matted regions can have a peak-to-valley height which increases toward the distal end of the optical fiber and/or a decreasing diameter.

A cladding tube—for example, matted—which scatters the laser radiation can be provided coaxially to the light waveguide arrangement.

A protective covering is necessary because the optical fiber is highly susceptible to breakage due to the partial matting or surface roughening. It can be formed in a cost-effective manner by a precision glass or hard-plastic hollow needle which is sealed at the end and is secured to the mechanically-fixed part of the light waveguide or hollow needle. In an advisable, sturdy embodiment of the catheter or hollow needle, the protective covering surrounds the entire front part of the catheter or needle and has openings for the exit of the fluid which scatters the laser radiation into the tissue.

The course of the temperature field propagation in the treated tissue can be monitored purposefully through continuous observation of the therapy area using a sonographic device, in which echoes can additionally occur in the blood vessels adjacent to the area, depending on the temperature, if the temperature here exceeds a value of 55° C., and the $CO_2$ dissolved in the blood is expelled intermediately and further echoes occur if water vapor bubbles form intermediately in the aqueous component of the light-scattering fluid when a temperature of 95° C. is exceeded.

Furthermore, an X-ray contrast medium can be added to the fluid, and a radiological observation of the formation and status of the deposit is performed.

Figure 1B:
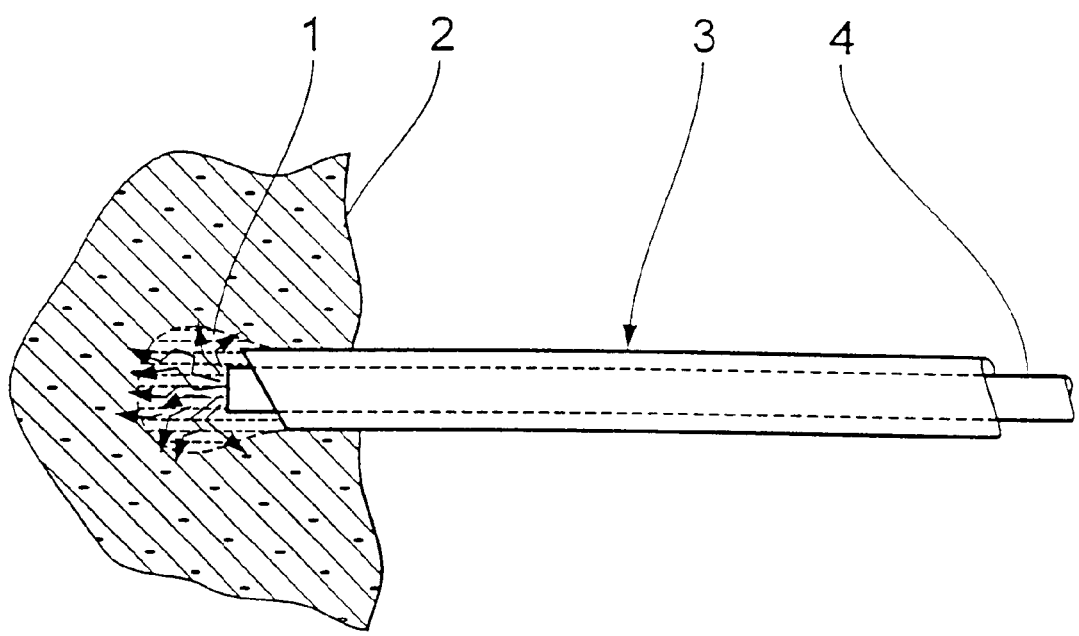
Figure 1C:
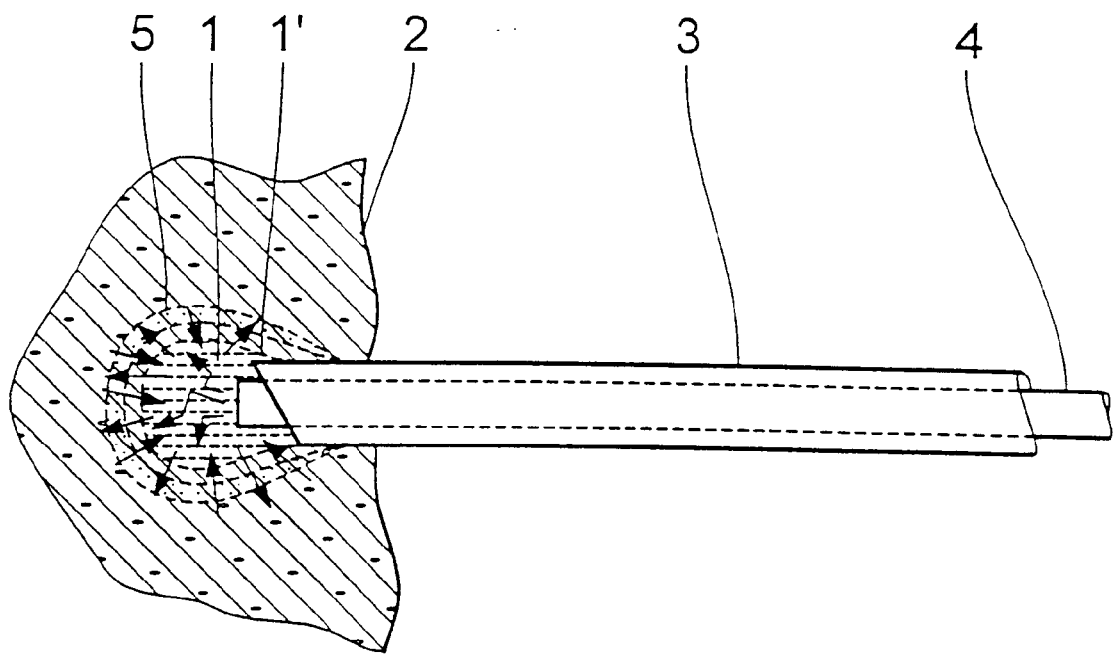
Figure 1D:
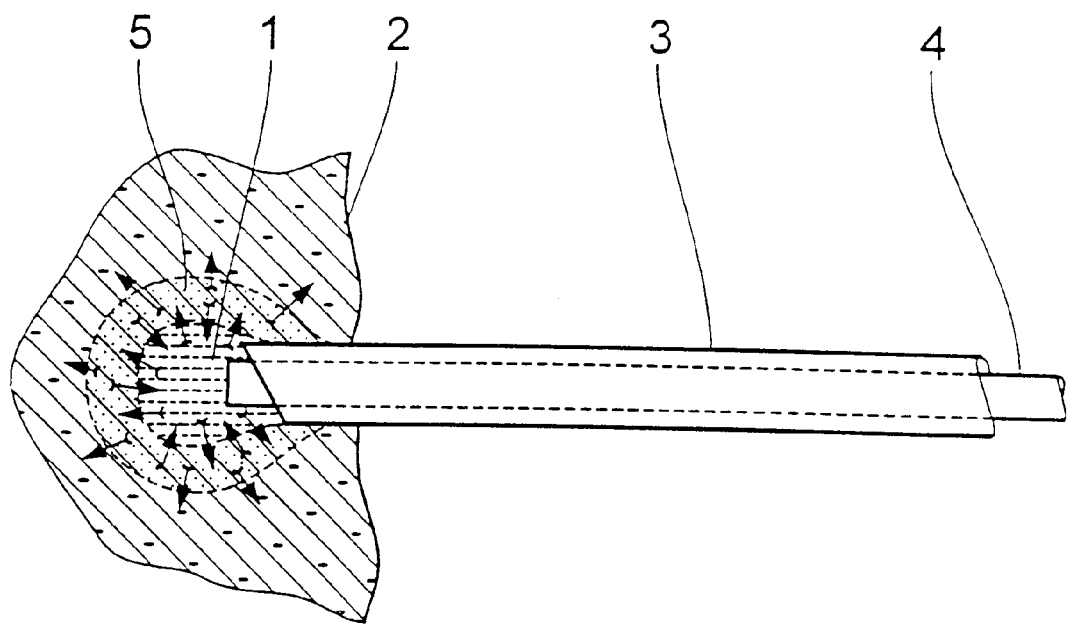
Figure 2:
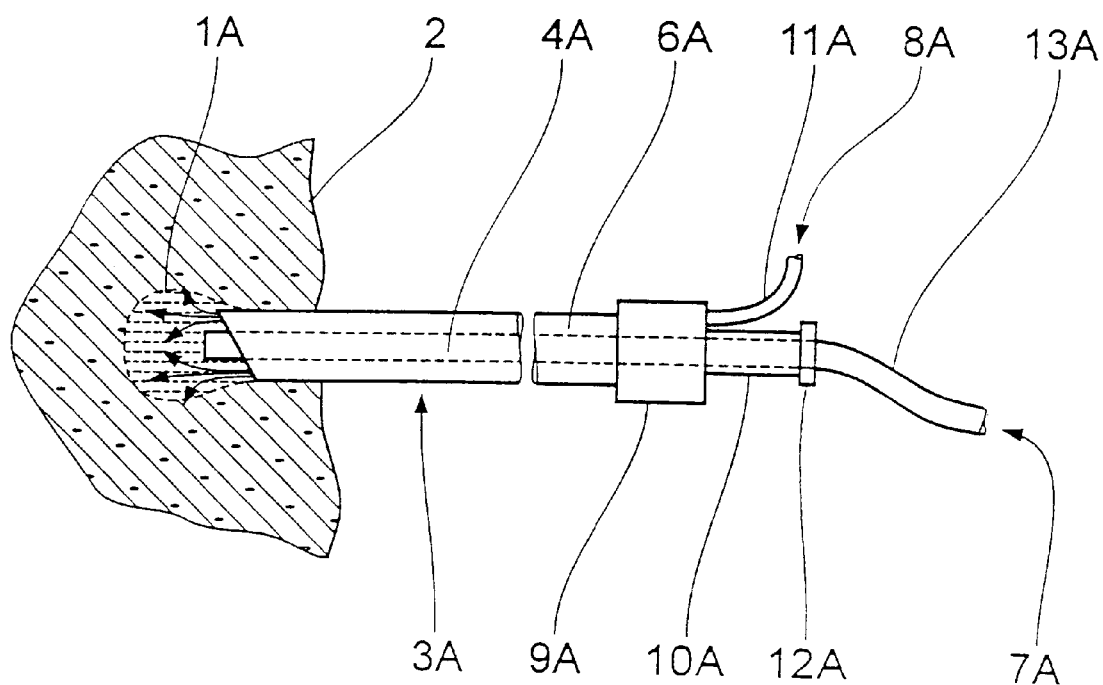
Figure 3:
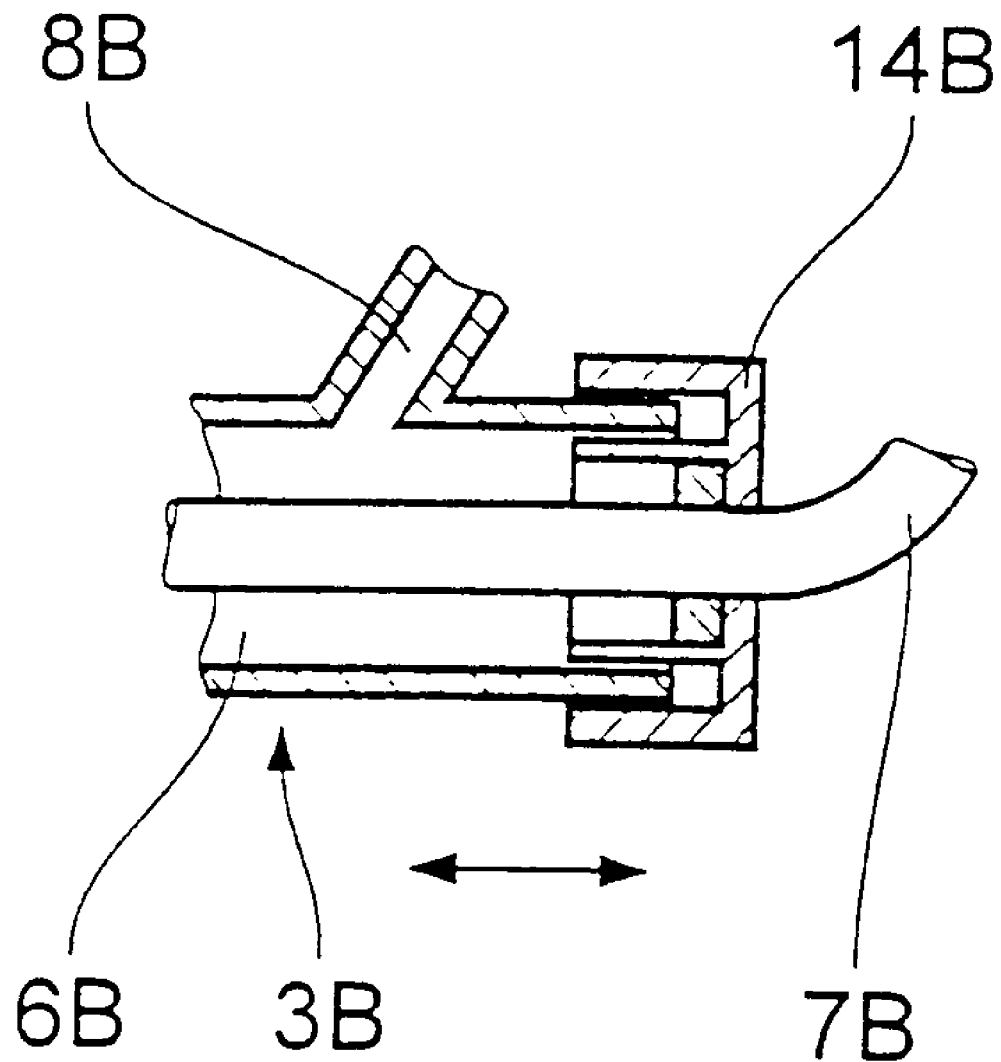
Figure 4:
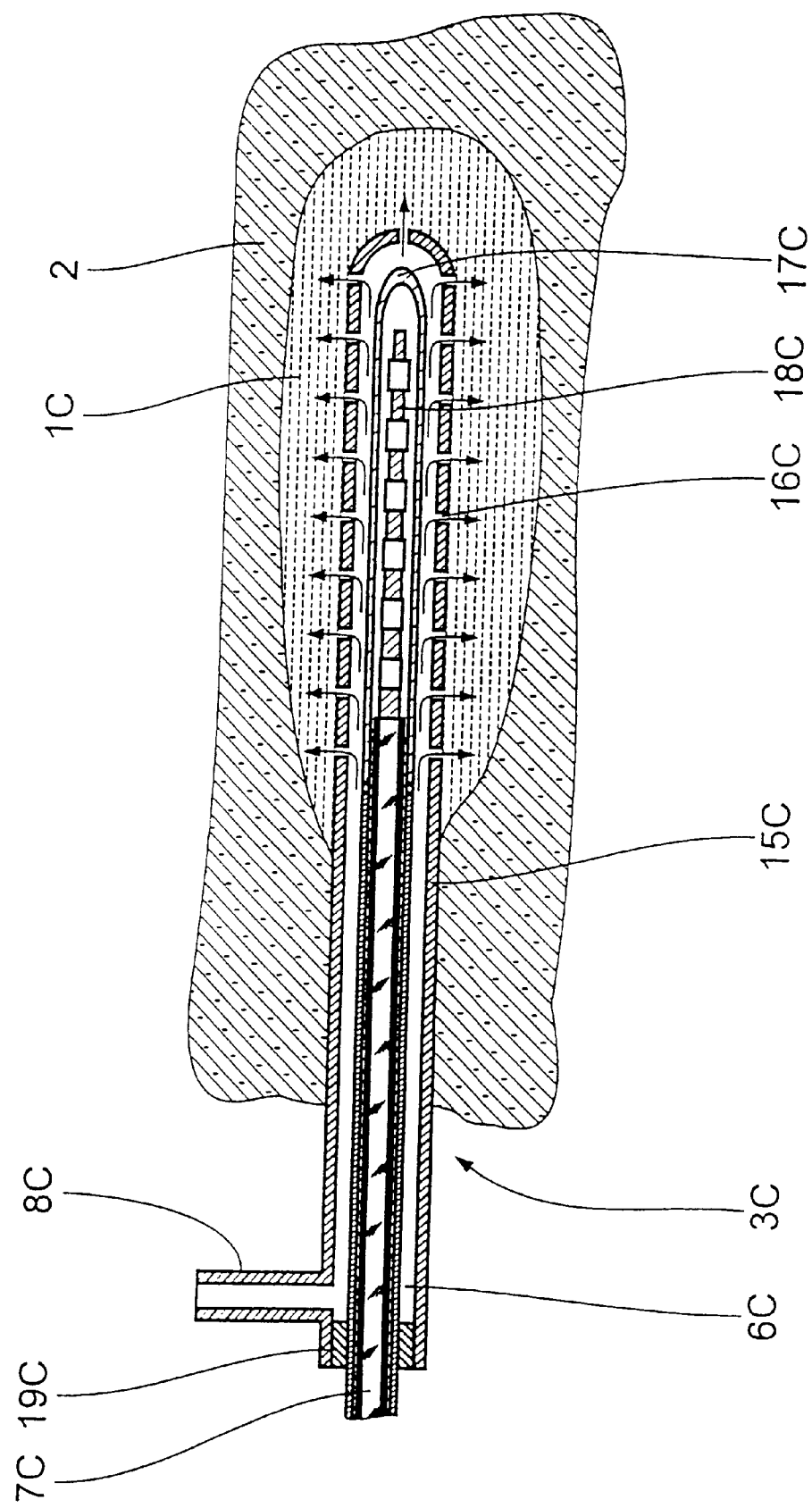
Figure 5:
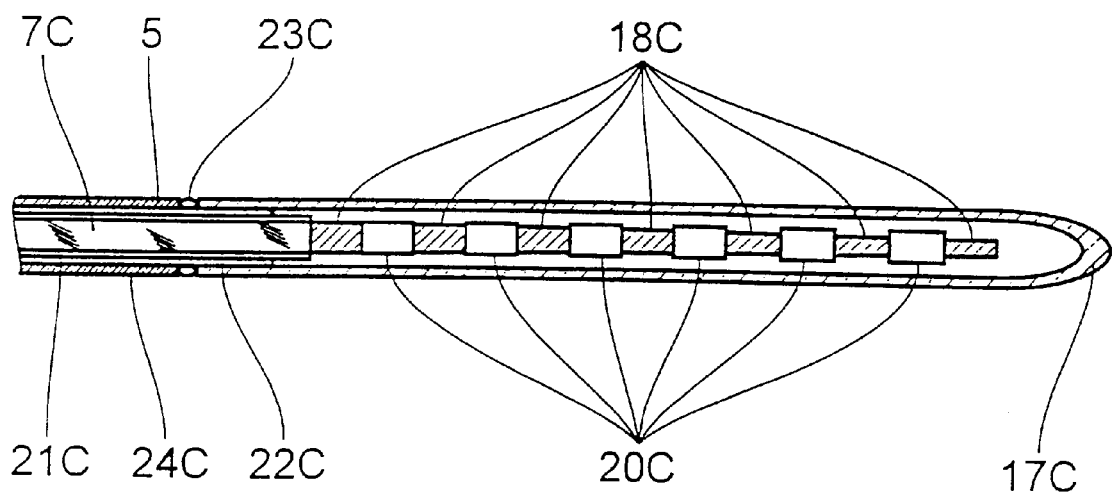
Figure 6:
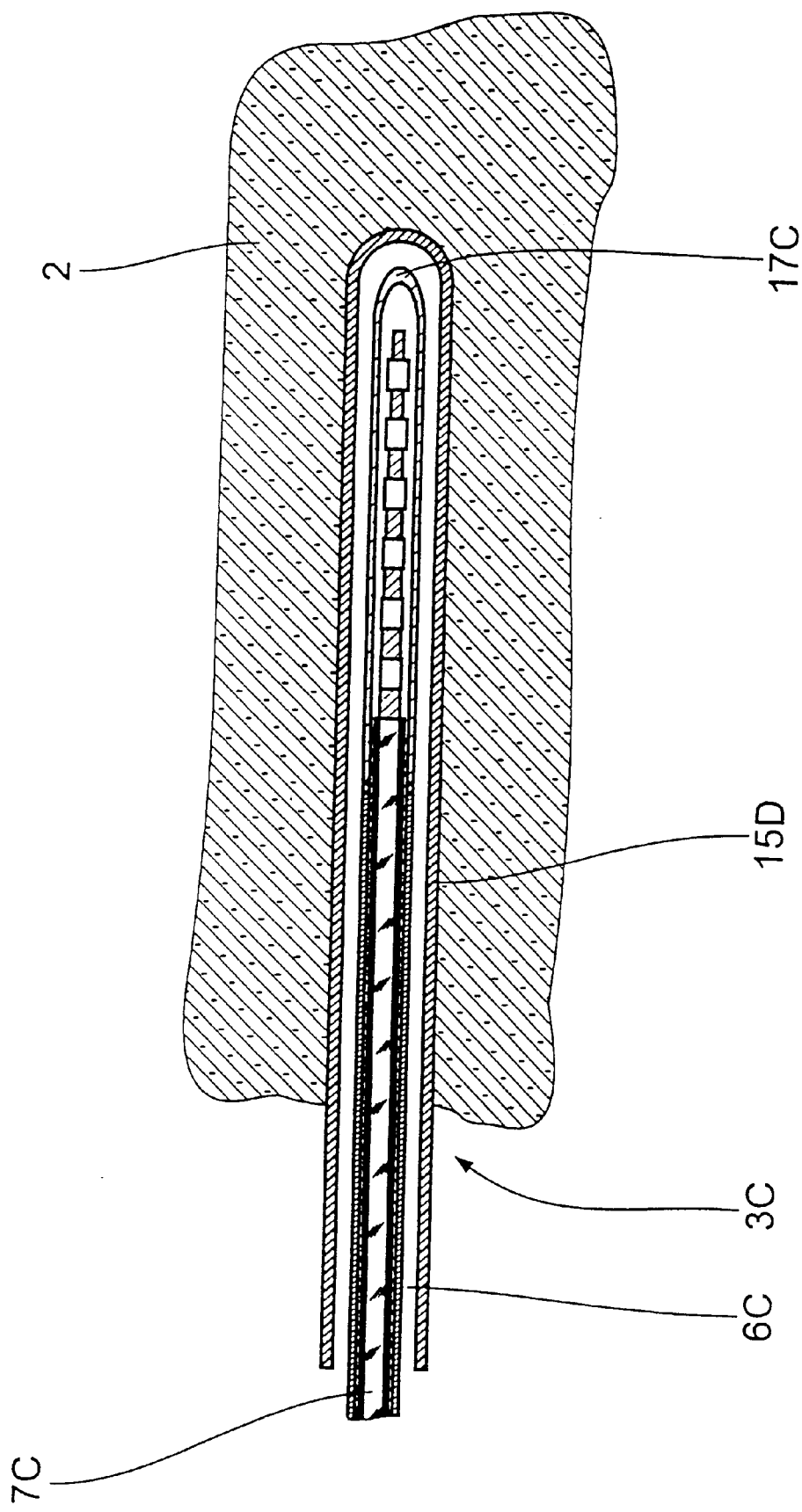
Figure 7:
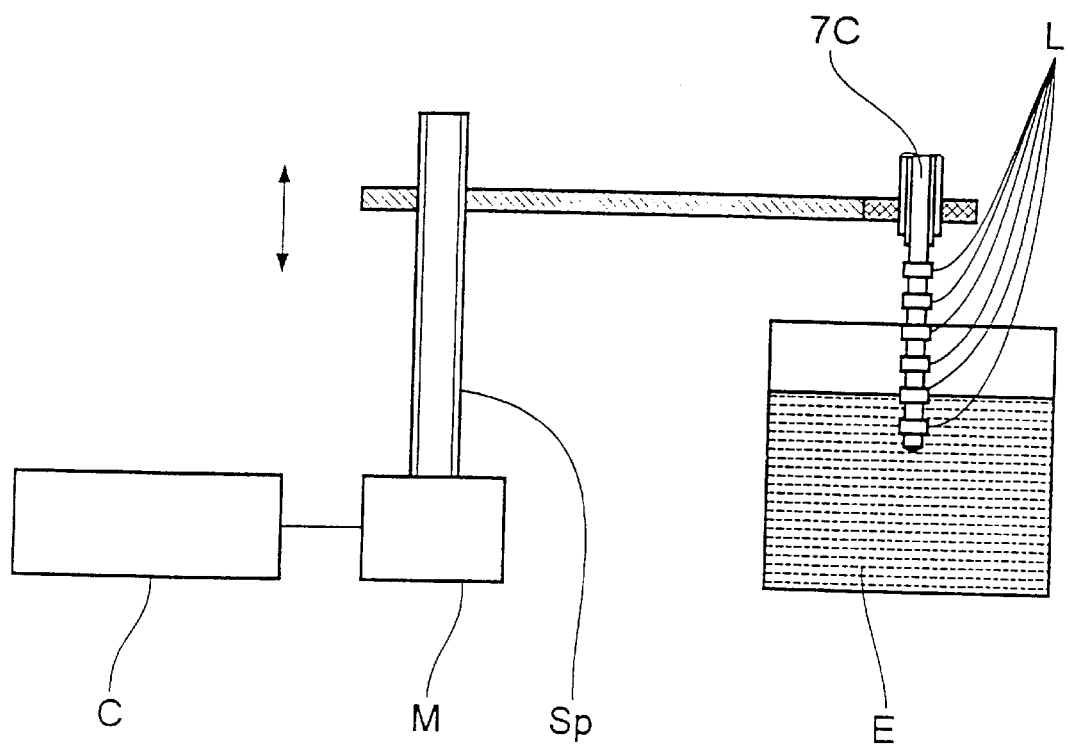

Advantageous modifications of the invention are characterized in the dependent claims or described in detail below, along with the description of the preferred embodiment of the invention, in conjunction with the figures. Shown are in:

FIGS. 1a through 1d schematic representations for explaining an embodiment of the method according to the invention, FIG. 2 a further schematic representation for explaining a modified embodiment of the method according to the invention and an apparatus for performing the method, FIG. 3 a schematic, cutout representation (in cross-section) of a further modified apparatus for performing the method according to the invention, FIG. 4 a simplified representation of a further embodiment, partly in section, FIG. 5 a detailed representation of the apparatus shown in FIG. 5 [sic], FIG. 6 a simplified representation of a further embodiment, partly in section, and FIG. 7 a schematic representation of a method of producing the light waveguide arrangement used in the embodiments according to FIGS. 4 through 6.

FIGS. 1a through 1d schematically illustrate how a fluid deposit 1 is created in a body tissue section 2 by means of a hollow needle 3, how laser radiation coupled into the deposit 1 is scattered by way of a fiber-optical light guide inside the hollow needle 3, and how a coagulation necrosis 5 results according to an embodiment of the method of the invention.

FIG. 1a schematically clarifies the general procedure of inserting a hollow needle 3 into the body tissue section 2 in order to perform the method: first, access into the center of the tissue area to be obliterated is gained with a probing wire or probing needle S. A dilator D is subsequently inserted by way of the probing needle S, the dilator D and finally the hollow needle 3 by way of the dilator D. Depending on the size of the necrosis focus to be created, a plurality of dilators can also be inserted in a plurality of steps, and the last one can simultaneously be the needle which guides the laser and/or fluid for the further steps, as described in more detail below.

In the phase shown in FIG. 1b, first viscous scattering fluid was injected into the tissue 2 by way of the hollow needle 3, and the spatially-defined fluid deposit 1 was formed therein, and the coupling-in of laser radiation into the deposit began. The photons of the laser radiation are—as symbolized by zigzagging arrows—scattered in the quasi-absorption-free scattering fluid of the deposit 1 and into the tissue 2. Consequently, a first virtual increase in volume is achieved in the transfer of energy into the tissue to be treated.

In the phase shown in FIG. 1c, at the phase border 1' of the deposit, the scattering fluid has a cooling effect with respect to the tissue, so that a coagulative effect primarily propagates in the depth of the tissue, and the coagulation layer 5 forms at a distance from the deposit 1. This means a further virtual increase in the active application volume during energy transfer. At the same time, a warming of the quasi-absorption-free scattering fluid deposit 1 takes place due to heat conduction—an energy exchange thus takes place in the boundary layer region symbolized by straight arrows in the figure.

In the phase shown in FIG. 1d, the laser radiation is shut off. The heated total volume of the interactive partial volumes effects an optimum inward expansion of the coagulation necrosis 5, that is, toward the deposit 1, as well as an outward expansion, that is, into the depth of the tissue 2 (clarified by arrows which become thicker at the end).

Control of this thermal obliteration of tissue volumes is effected with the use of two surprisingly discovered phenomena:

1. In vital biological tissues which have blood flow, the metabolism dictates that a specific quantity of $CO_2$ always be dissolved in the blood; it has been seen that the solubility product of $CO_2$ in whole human blood is of such a nature that an intermediary expulsion occurs at temperatures above 55° C., but is reversible if this temperature is not met, i.e., deeper in the tissue volume. This expulsion of $CO_2$ in the blood can be proven in a simple manner by the indication of a change in contrast by the ultrasound system used for original positioning of the guide needle, so that the 55° C. front of the temperature field propagation can consequently be followed in real time.

2. Furthermore, it has been seen that water vapor is also formed at a temperature of approximately 95° C. with the used scattering fluid, a viscous water-glycerine-oil mixture or water-methyl cell mixture, so that the consequently-resulting gas bubbles can easily be observed in the fluid deposit in the ultrasound image in order to avoid exceeding the boiling point. When the solubility product is not attained, the water vapor returns immediately to solution, and does not represent an embolism threat.

In a modification shown schematically in FIG. 2, a hollow needle 3A inserted into a body tissue 2 is double-channeled in the form of an integrated fluid light guide such that it has a coaxially-extending inside channel 4A which is surrounded concentrically by an outside channel 6A. In this instance, the inside channel 4A serves as a fluid light guide through which an optically-transparent component 7A of the scattering fluid is conveyed. The outside channel 6A guides a scattering or more highly-viscous component 8A of the fluid toward the distal end of the hollow needle 3A, where a fluid deposit 1A is formed from the two components.

The proximal end of the hollow needle 3A has a branching element 9A, from which a supply line 10A extends toward the inside channel 4A and a supply line 11A extends toward the outside channel 6A.

The inside channel serves in the puncturing phase as a guide shaft for the probing needle for positioning the hollow needle in the region to be treated. The hollow needle 3A is positioned by a puncturing needle, the puncturing needle is subsequently removed and the optically transparent fluid component is applied by way of the supply line 10A and the inside channel 4A, and in a second step the resulting fluid deposit 1A is enriched with scattering medium by way of the line 11A and the outside channel 6A. At the same time, an optical fiber 13A is coupled to the fluid column by way of a compressed seal inside the central channel 4A of the puncturing needle, which then serves as a fluid light guide when laser radiation is coupled in by way of the optical fiber 13A.

In a preferred embodiment, a mixture of 80% glycerine and 20% water is used as the transparent carrier fluid, the mixture having a refractive index which is essentially identical to the refractive index of the coupling, laser-light-guiding optical fiber. The light-scattering medium comprises a 2 to 5% oil-water emulsion, for example Intralipid, in a suitable dilution. In this modification, as dictated by structure, there is no longer any contact at all between optical fiber and tissue with the risk of carbonization; rather, the introduction of radiation into the tissue and the resulting deposit are effected a priori by only the fluid itself. A thorough mixing of the two components of scattering medium and transparent carrier substance is effected independently by the occurring thermal fluctuations when the components are acted upon by laser radiation, with the consequence that the laser light exiting the fluid light guide does not directly enter a zone of high scatter, but is gradually scattered to a greater extent in the deposit with an increasing radiation depth. This again leads to an improved introduction of scattered light into the tissue volume to be treated.

FIG. 3 shows a detailed representation in longitudinal section of the end section of a hollow needle 3B which is modified with respect to the hollow needle 3A according to FIG. 2 and includes a throughgoing optical fiber 7B (not shown in the figure) which penetrates up to the distal end. An outside channel 6B which is connected by way of a lateral projecting part 8B to an apparatus (not shown) for the supply of scattering fluid, is sealed by an axially displaceable, fluid-tight sealing cap 14B at the proximal end of the hollow needle 3B. The optical fiber 7B is fixedly connected to the sealing cap 14B. An extension of the fiber end out of the distal end of the hollow needle 3B by approximately 1 to 2 mm and into a scattering fluid deposit created there in advance is possible by means of an axial displacement of the sealing cap (or, in an embodiment which includes a union nut, a rotation of the cap) after the insertion of the hollow needle with the fiber end being pre-adjusted to align with the end of the hollow needle.

FIG. 4 shows a simplified representation in longitudinal section of a further hollow needle or catheter 3C for producing large-volume, longitudinally-extending coagulation necroses in body tissue 2. The catheter 3C has an outside catheter body 15C of transparent plastic which has an essentially cylindrical shape and is closed at its distal end so as to be rounded, and is provided with openings 16C over a distal region a few cm long. An inside hollow glass needle 17C is disposed coaxially to the outer catheter body 15C and in its interior 6C, and extends nearly to the distal end of the outside catheter body 15C and is likewise closed at its distal end. The outside catheter body has a fluid supply 8C which branches off laterally near its proximal end, which is sealed with a plug 19C.

The hollow glass needle 17C receives an optical fiber 7C which is provided in its end region of approximately 3 cm long with a plurality of annular, equidistantly-spaced matting regions 18C. The optical fiber 7C is connected (not illustrated in the figure) at its proximal end to a laser radiation source.

By means of paraxial supply of medium-viscous to highly-viscous scattering fluid by way of the supply 8C, which is guided into the surrounding tissue via the catheter interior 6C and the openings 16C, a longitudinally-extending fluid deposit 1C is formed which surrounds the end region of the catheter. When laser radiation is subsequently supplied, it is sequentially or periodically coupled out at the matted rings and at the end face of the fiber 7C.

Surprisingly, in connection with the scattering fluid deposit located at the edge, it is possible for the first time to attain a virtually uniform distribution of the laser radiation over a long, cylindrical segment in the tissue without a considerable fluid volume of the biocompatible scatter light fluid. The extension of the scatter light application, which therefore first becomes possible in accordance with the invention, permits simultaneous application of higher laser powers, so that, for example, for the above-cited treatment of a prostate lobe having a longitudinal expansion of up to 5 cm and a diameter of 2 cm, and an application of 15 to 20W laser light power, radiation times of only 10 minutes are necessary in order to achieve the desired therapy results. The combination of paraxially-supplied scattering fluid and coupled-in laser radiation which is distributed in the longitudinal direction of the catheter during treatment ensures that the radiation which is periodically scattered non-homogeneously out of the fiber toward the tissue is homogenized, and the outcome is a calculable and uniform treatment result.

FIG. 5 shows a more precise, enlarged representation of the inside hollow needle 17C with the optical fiber 7C according to FIG. 4. It can be seen how matted rings 18C having a longitudinal ratio of 1:1 and untreated fiber segments 20C alternate in the end region of the fiber freed from its cladding 21C and coating 22C. The matted rings 18C have a diameter which decreases toward the end of the fiber, or an increasing peak-to-valley height. The hollow glass needle 17C, which can be clear or matted, and can also alternatively be made of plastic (for example, polycarbonate), is adhered, proximally to the matting region, to the coating 22C of the fiber and an MRI marker 24C sheathing it by an adhesive 23C.

FIG. 6 illustrates a modification of the arrangement shown in FIGS. 4 and 5. Whereas the designs of the inside hollow needle and the optical fiber correspond to those in the above-described figures, and are therefore provided with the same reference numerals as in FIG. 4, 17C and 7C, respectively, a closed catheter body 15D of the material which scatters the laser radiation is provided here. In this design, a scattering fluid deposit can be extensively or, possibly, entirely omitted, or the catheter can be inserted into a deposit which was created in advance with other means.

FIG. 7 shows an option of producing the annular structure in the distal end region of the optical fiber 7C: the end of the base fiber which is free from coating and cladding is coated with rings L made of an acid-proof lacquer (etching lacquer) and the fiber is dipped in stages into an etching fluid E with the use of a control C, a motor M and a spindle-holding element Sp, with the surface of the fiber being etched in the uncoated regions. Since the amount of time spent in the etching fluid decreases with an increasing distance of the etched regions from the end of the fiber, the etching depth also decreases in this direction, by means of which the desired course of the peak-to-valley height or effective fiber diameter is achieved. The lacquer rings are removed following etching.

The invention is not limited in its embodiment to the above-disclosed exemplary embodiments. Rather, a number of variations is conceivable which makes use of the illustrated solution, even in embodiments of principally different natures.

What is claimed is:

1. A process for thermally obliterating biological tissue by means of laser radiation transmission through a light waveguide, comprising the steps of
   introducing a light waveguide's distal end into a biological tissue through a multichannel hollow needle and apparatus;
   injecting a biocompatible fluid, having a selected viscosity, into said tissue near said distal end, wherein said fluid essentially scatters said laser radiation but does not absorb said laser radiation;
   creating a deposit of said scattering fluid surrounding said lightguide's distal end which functions as an exit surface of said laser radiation;
   creating said scattering fluid deposit substantially from two components, an essentially transparent component and a highly light-scattering component, wherein said components are injected into said tissue through separate channels within a concentric double channel hollow needle such that said transparent component is injected through an inner channel and said highly light-scattering component is injected through a concentric outer channel enveloping said transparent component,
   wherein said viscosity of said scattering fluid has been selected to diffuse said scattering fluid within said tissue to be thermally obliterated prior to and during laser irradiation in such a way that said scattering fluid deposit maintains a stable structure for the duration of treatment; and
   transmitting said laser radiation through said waveguide and into said scattering fluid within said biological tissue to coagulate and to cause necrosis of said tissue.

2. A process according to claim 1 having the additional steps of
   forming said scattering fluid from a mixture of oil, water and glycerin; and
   adjusting said mixture to contain 0.1 to 0.2% oil, 10 to 50% water and 50 to 80% glycerin depending on said tissue to be obliterated and required scattering properties for said fluid.

3. A process according to claim 1, shaving the additional steps of:
   forming said scattering fluid from a mixture of methyl cellulose and water; and
   adjusting said mixture's components to contain 70 to 99% methyl cellulose and 1 to 30% water depending on required viscosity and scattering properties for said fluid.

4. A process according to claim 1, having the additional steps of:
   forming said transparent component of said fluid from a mixture of glycerin and water, preferably in a ratio of 80:20; and
   forming said highly light-scattering component from a mixture of oil and water, preferably with 1 to 5% oil.

5. A process according to claim 1, wherein said fluid contains hyaluronic acid and/or Intralipid.

6. A process according to claim 1, shaving the additional step of:
   after injecting and forming said scattering fluid deposit, displacing said light waveguide in said distal end's direction so that said lightguide enters said scattering fluid deposit by a preselected amount dependent on said tissue area to obliterated.

7. A process according to claim 1, wherein creating said scattering fluid deposit is performed so as not make said deposit spherically symmetrical but rather a longitudinally-extended shape, such as an essentially ellipsoidal or cylindrical shape.

8. A process according to claim 1, having the additional step of:
   monitoring temperature created in said tissue to be obliterated and its surroundings and said temperature's propagation throughout a therapy area by means of a sonographic device, wherein echoes occur in blood vessels adjacent to said therapy area depending on said temperature; at temperature values above 55° C. echoes arise from previously dissolved $CO_2$ being expelled intermediately and at temperatures above 95° C. echoes arise by formation of water vapor bubbles appearing intermediately within said aqueous component of said scattering fluid.

9. A process according to claim 1, having the additional steps of:
   adding an X-ray contrast medium to said scattering fluid; and
   monitoring progress of said process by radiological observations.

10. A process according to claim 1, wherein said transmitting of laser radiation to said biological tissue is carried out by using said transparent component of said fluid within said inner channel as a light waveguide.

11. A process according to claim 10, wherein said transmitting of laser radiation and said injecting of said transparent component of said fluid into said inner channel occur in at least overlapping time periods.

* * * * *